(12) United States Patent
Senini

(10) Patent No.: US 6,866,505 B2
(45) Date of Patent: Mar. 15, 2005

(54) SELF-ENGAGING ORTHODONTIC BRACKET

(76) Inventor: Robert J. Senini, 2510 Navarra Dr., #502, Carlsbad, CA (US) 92009

(*) Notice: Subject to any disclaimer, the term of this patent is extended or adjusted under 35 U.S.C. 154(b) by 0 days.

(21) Appl. No.: 10/438,565

(22) Filed: May 14, 2003

(65) Prior Publication Data
US 2004/0229184 A1   Nov. 18, 2004

(51) Int. Cl.[7] .............................................. A61C 7/00
(52) U.S. Cl. ........................................................ 433/10
(58) Field of Search ............................. 433/10, 11, 13, 433/14, 17, 24

(56) References Cited

U.S. PATENT DOCUMENTS

| | | | |
|---|---|---|---|
| 2,011,575 A | * | 8/1935 | Ford ............................ 433/10 |
| 2,921,371 A | * | 1/1960 | Wallshein ..................... 433/13 |
| 3,238,619 A | * | 3/1966 | Brunson et al. .............. 433/13 |
| 3,458,031 A | * | 7/1969 | Hoffman ........................ 433/3 |
| 3,772,787 A | | 11/1973 | Hanson |
| 4,077,126 A | | 3/1978 | Pletcher |
| 4,171,568 A | * | 10/1979 | Forster ......................... 433/10 |
| 4,197,642 A | | 4/1980 | Wallshein |
| 4,248,588 A | | 2/1981 | Hanson |
| 4,344,642 A | | 8/1982 | Goth |
| 4,371,337 A | * | 2/1983 | Pletcher ....................... 433/10 |
| 4,419,078 A | | 12/1983 | Pletcher |
| 4,559,412 A | | 12/1985 | Howard et al. |
| 4,561,844 A | | 12/1985 | Bates |
| 4,634,661 A | | 1/1987 | Cavallaro |
| 4,655,708 A | | 4/1987 | Fujita |
| 4,712,999 A | | 12/1987 | Rosenberg |
| 4,786,242 A | | 11/1988 | Barsk |
| 5,439,378 A | | 8/1995 | Damon |
| 5,466,151 A | | 11/1995 | Damon |
| 5,474,445 A | | 12/1995 | Voudouris |
| 5,474,446 A | | 12/1995 | Wildman et al. |
| 5,857,850 A | | 1/1999 | Voudouris |

FOREIGN PATENT DOCUMENTS

FR          2710830 A1  *  4/1995

* cited by examiner

*Primary Examiner*—Todd E. Manahan
(74) *Attorney, Agent, or Firm*—Henri J. A. Charmasson; John D. Buchaca

(57) ABSTRACT

An orthodontic bracket for securing an arch wire to the labial area of a tooth comprises a plunger having a lateral notch dimensioned to capture a section of the arch wire. A dual-positioned detent mechanism alternately holds the plunger in a labial, open position exposing the notch and a lingual locked position wherein the section of arch wire captured by the notch is securely held in a diametral slot cut into the bracket.

17 Claims, 2 Drawing Sheets

SELF-ENGAGING ORTHODONTIC BRACKET

FIELD OF THE INVENTION

This invention relates to orthodontic brackets used to secure a corrective arch wire to the labial face of a tooth.

BACKGROUND OF THE INVENTION

A common orthodontic technique consists in ligating an arch wire to a bracket mounted against a tooth by means of elastomeric or metal ligature. The ligature is stretched around respective undercuts of gingival and occlusal tie wings so as to overlay the arch wire at mesial and distal ends of the bracket.

The ligating procedure requires carefully stretching an elastomeric ligature or wrapping and twisting a metal ligature around the tie wings utilizing appropriate orthodontic instruments. The complex ligation procedure contributes to lengthy chair-time. The ligatures tend to loosen up in time diminishing the effectiveness of the arch wire correction. The ligatures also trap food particles in areas of the bracket which are difficult to clean and tend to hide infectious bacteria and viruses such as those of hepatitis B or HIV creating an exposure hazard for the clinician. Moreover, sharp metal ligatures can cause discomfort and even tissue irritation that can lead to infection.

In an effort to overcome the aforesaid disadvantage of ligatures, a number of alternate arch wire securing mechanisms have been proposed such as the one disclosed in U.S. Pat. Nos. 3,772,787; 4,077,126; 4,197,642; 4,248,588; 4,344,642; 4,419,078; 4,559,412; 4,561,844; 4,634,661; 4,655,708; 4,712,999; and 4,786,242.

These so-called pre-engaging or self-engaging orthodontic brackets rely on clasping, sliding or clamping mechanisms which lack the ease of access and of operation that most clinicians desire.

The present invention results from an attempt to devise a self-engaging orthodontic bracket that can be locked and unlocked with ease upon a section of corrective arch wire.

SUMMARY OF THE INVENTION

The principal and secondary objects of this invention are to provide a versatile and easy to use orthodontic bracket that can be locked around a section of corrective arch wire by a simple pushing movement and can be similarly unlocked without the use of any complex tool, the bending of resiliently flexible components and other complex manipulation.

These and other valuable objects are achieved by a bracket securable to the labial surface area of a tooth and defining a well into which a plunger can be secured at alternate locking and unlocking positions by a simple detent mechanism. The plunger has a lateral notch that lines up with a diametral slot cut across the rim of the well and can alternately be held in a notch-exposing position outside the well whereby a section of an arch wire can be nested into the notch then moved inwardly into a locking position where access to the notch is occluded and the section of arch wire is firmly held in a passageway defined by aligned portions of the notch and slot.

DESCRIPTION OF THE PREFERRED EMBODIMENT OF THE INVENTION

Figures 1, 2:
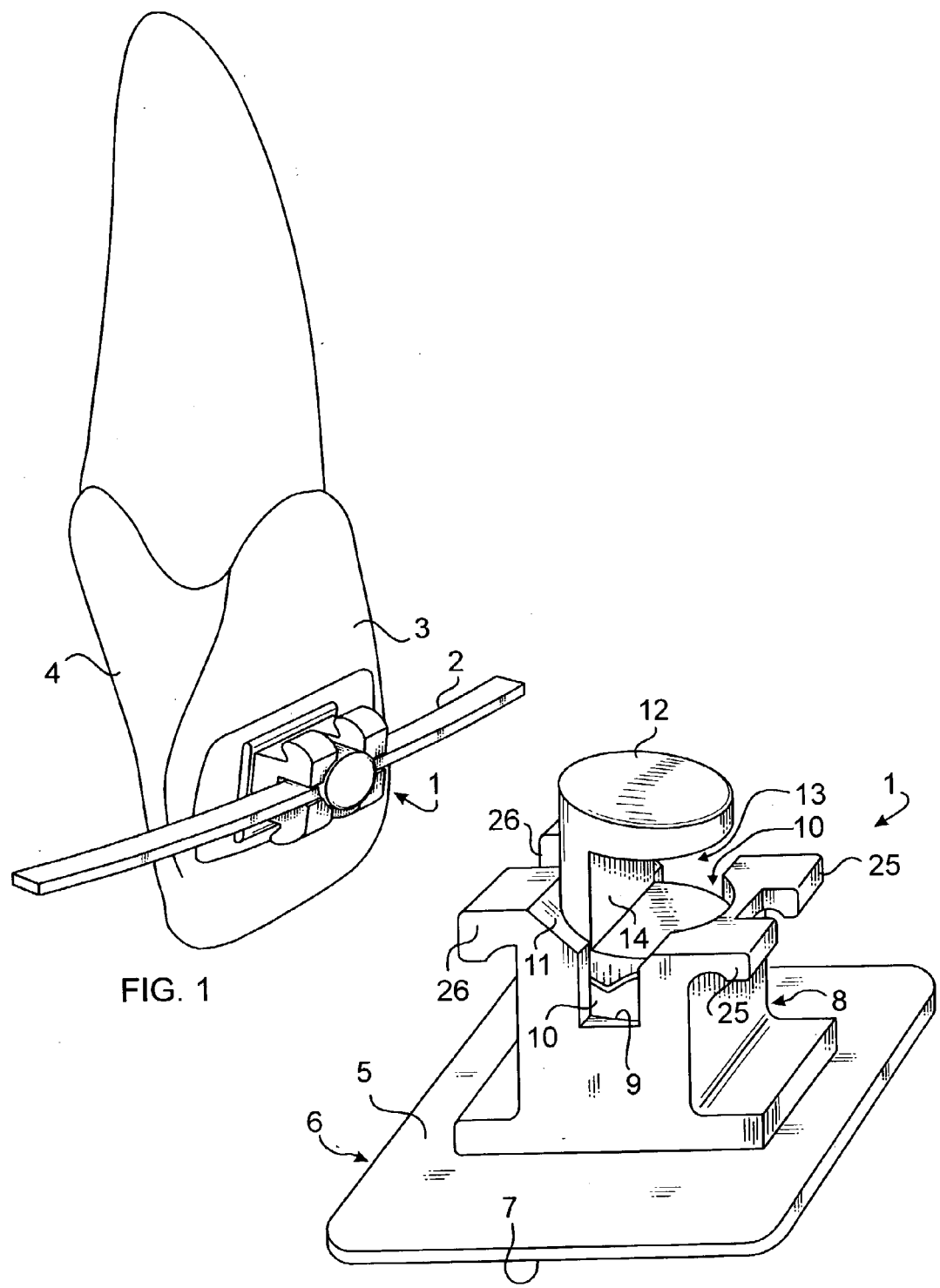
FIG. 1 is a perspective view of a self-engaging orthdontic bracket in use on a tooth.
FIG. 2 is a perspective view of the bracket.

Referring now to the drawing, there is shown in FIG. 1, a self-engaging orthodontic bracket 1 according to the invention securing a corrective arch wire 2 against the labial surface 3 of a tooth 4.

As shown in FIG. 2, the bracket 1 is mounted on the distal, labial face 5 of a pad-forming base 6 whose proximal, lingual face 7 is shaped and dimensioned to intimately adhere to the labial surface area 3 of the tooth. The bracket comprises a substantially cubical block or body 8 projecting distally, i.e., in a labial direction from the base, and having a side dimension of approximately 3 to 4 millimeters. A cylindrical well 9 is axially bored through the length of the body 8 in an axial direction substantially orthogonal to the labial and lingual faces of the pad.

A rectangular slot 10 is diametrally cut across the rim 11 of the well on the distal side of the body. A cylindrical post or plunger 12 is slidingly and intimately engaged into the well. The post has a lateral notch 13 whose innermost section 14 is aligned with the slot 10.

Figure 3:
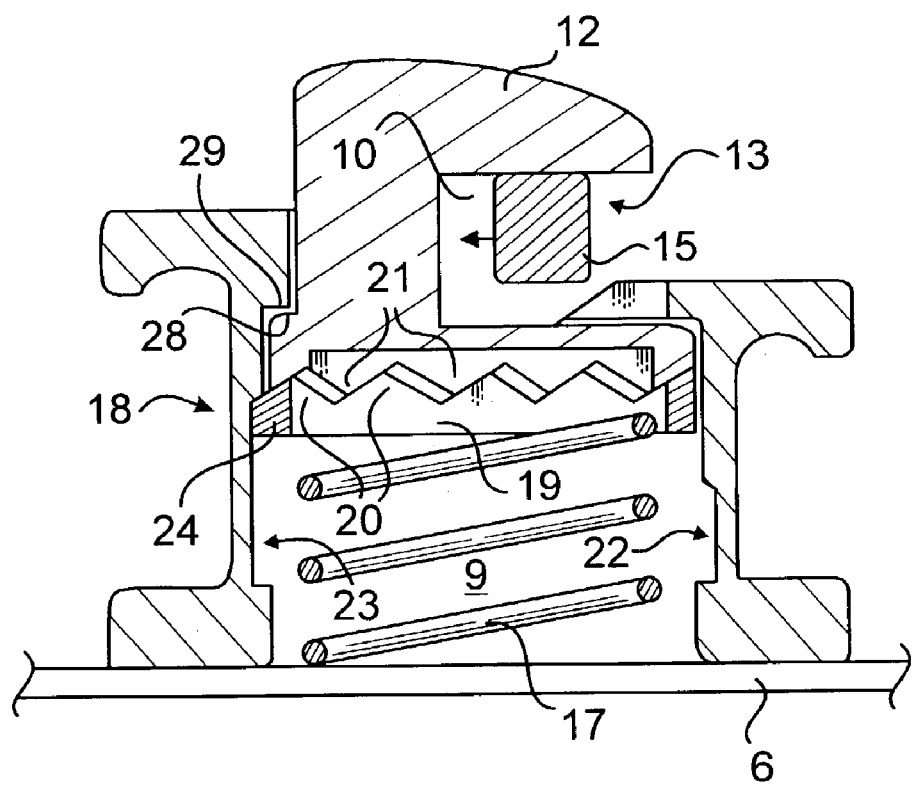
FIG. 3 is a median cross-sectional view of the bracket in the open position.

As more specifically illustrated in FIG. 3, the lateral notch 13 is shaped and dimensioned to accept a section 15 of the corrective arch wire 2.

Figure 4:
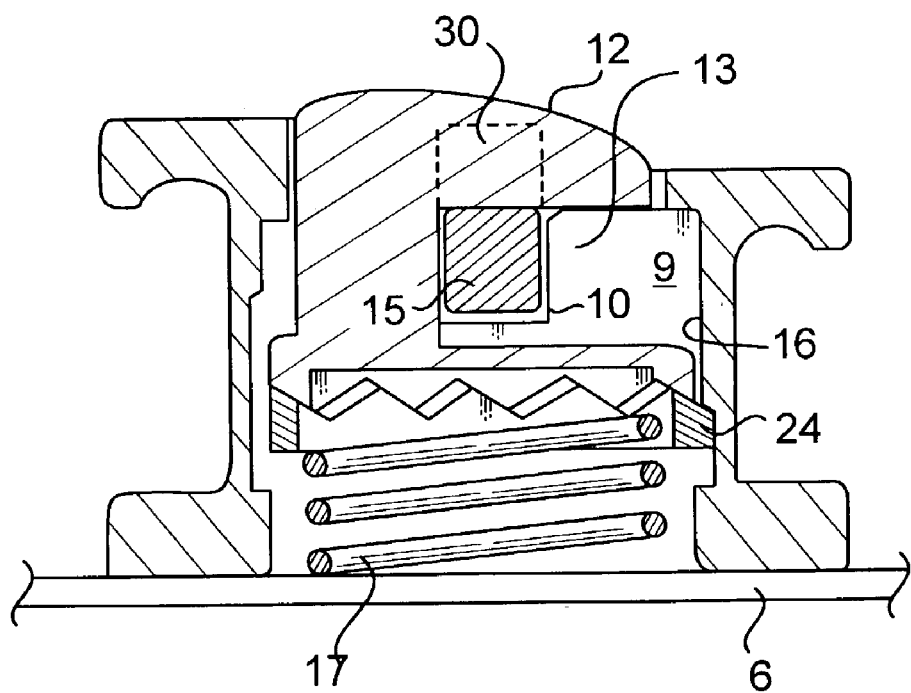
FIG. 4 is a median cross-sectional view of the bracket in the closed position.

As more specifically illustrated in FIG. 4, the slot 10 is also dimensioned to capture the arch wire section 15.

In the open or unlocked position of the bracket illustrated in FIG. 3, the post 12 is shown in its most distal position exposing beyond the distal side of the body 8 the opening of the notch 13 that provides access for the arch wire section 15. In the locked or closed position of the bracket illustrated in FIG. 4, the post 12 has been translated into the well, and the access to the notch 13 is occulted by the wall 16 of the well. A coil spring 17 compressed into the well between the post 12 and the pad 6 resiliently biases the post toward its most distal position illustrated in FIG. 3.

The post is alternately held in the notch-exposing position of FIG. 3 and the notch-occulting position of FIG. 4 by a dual-position detent mechanism not unlike the one commonly used in connection with ballpoint pens. The detent mechanism 18 comprises an indexing ring 19 whose upper rim is crowned by a series of triangular teeth 20 meshing with similar teeth 21 cut in the periphery of the proximal, inner end of the post 12. A series of alternating, axially oriented short indentations 22 and long indentations 23 are practiced around the circular surface of the inner wall 16 of the well. These long and short indentations are successively engaged by one or more keys 24 on the outer periphery of the indexing ring 19 as the ring is rotated by successive sliding movements of the post up and down the well. When a key 24 is captured by a short indentation 22, the post 12 is locked in the closed position of FIG. 4. When a key is captured by one of the long indentations 23, the post is allowed to rise to the open position of FIG. 3. In the locked position of FIG. 4, the slot 10 and notch 13 line up to define a transversal passageway that can intimately capture the section 15 of the arch wire.

A pair of spaced-apart tie wings 25 project laterally from the body 8 in an occlusal direction. A similar pair of spaced-apart tying wings 26 project laterally from the body in a gingival direction.

In assembling the bracket, the post 12 is first inserted into the well from the proximal side of the body 8 followed by the indexing ring 19 and spring 17 before securing the assembly to the pad 6. The distal translation of the post within the well is limited by abutting shoulders 28 and 29 formed in the peripheries of the post and distal area of the well respectively.

An equivalent embodiment of the bracket can be constructed by cutting a pocket 30, shown in dotted lines in FIG. 4, in the innermost distal area of the notch 13 and by eliminating the slot 10. The pocket cross-sectional dimensions are made commensurate with those of the arch wire section 15 so as to firmly hold the arch wire upon pushing the post to its proximal locking position.

It should be noted that another equivalent embodiment of the bracket can be implemented by mounting the post fixedly upon the pad 6 and allowing the surrounding body 8 to slidingly translate up and down around the post from a position exposing the notch 13 to one closing that notch. The same type of dual position detent mechanism used in the preferred embodiment can be conveniently adapted to immobilize the sliding body in both the open and closed position of the bracket. In the above described equivalent embodiments, the position of the wire is not altered by the movement of the post or body.

It can now be understood that a section of the corrective arch wire can conveniently be captured and held by the bracket through a simple procedure which consists in inserting the arch wire section into the exposed slot then pushing the post until it automatically locks into its proximal, innermost position. It should also be noted that the post-locking mechanism is self-contained and internal to the bracket itself. Accordingly, there is no exposed area that can cause irritation or collect food particles. The arch wire locking and unlocking maneuvers are relatively simple and do not require any undo force that could disrupt the alignment of the bracket. Moreover, the required forces are always orthogonal to the labial surface of the tooth.

While the preferred embodiments of the invention have been described, modifications can be made and other embodiments may be devised without departing from the spirit of the invention and the scope of the appended claims.

What is claimed is:

1. An orthodontic bracket, for securing a corrective arch wire to the labial surface area of a tooth, which comprises:
    a post associated with said bracket and having a lateral notch shaped and dimensioned to capture a section of said arch wire;
    a dual-positioned detent mechanism for alternately exposing an occluding access to said notch;
    a base having a face shaped and dimensioned to intimately adhere to said labial surface;
    wherein said post extends substantially orthogonally to said labial surface;
    a solid body having a distal side and a well in said distal side; and
    wherein said post is slidingly engaged into said well and is alternately positionable by said detent mechanism in a notch-exposing position outside said well and in a locking position within said well.

2. The bracket of claim 1, wherein said body has a slot cut in said distal side and diametrically intersecting said well; and
    in said locking position, portions of said notch and slot line up to define a passageway commensurate with said section of arch wire.

3. The bracket of claim 2, wherein said detent mechanism comprises a compression spring positioned within said well to bias said post toward said notch-exposing position.

4. The bracket of claim 3, wherein said detent mechanism further comprises:
    said well having a cylindrical wall section and a series of alternating short and long, axially oriented indentations in said well section;
    an indexing ring having at least one peripheral key shaped and dimensioned to alternatly engage said short and long indentations; and
    means, associated with said post, for incrementally rotating said ring with each sliding movement of said post into said well.

5. The bracket of claim 3, which further comprises a base pad having a first face shaped and dimensioned to intimately contact said surface area of the tooth.

6. The bracket of claim 5, wherein said detent mechanism is housed in a lingual section of said well proximate said pad.

7. The bracket of claim 1, which further comprises a pair of spaced-apart tie-wings projecting laterally thereupon in a gingival direction.

8. The bracket of claim 7, which further comprises a second pair of spaced-apart tie-wings projecting laterally therefrom in a occlusal direction.

9. An orthodontic bracket, for securing an arch wire to the labial surface area of a tooth, which comprises:
    a pad having a lingual first face shaped and dimensioned to intimately adhere to said area;
    a solid body projecting distally from a labial second face of said pad opposite said first face and having a distal side;
    said body defining a well axially orthogonal to said faces and having a rim on said distal side and a slot diametrally intersecting said well and extending from said rim over a distal portion of said body;
    said slot being shaped and dimensioned to engage a section of said arch wire;
    a plunger slidingly and intimately engaged into said well and having a peripheral wall surface and a notch cut radially into said wall surface;
    said notch having a portion aligned with said slot;
    resilient means for biasing said plunger toward a first labial resting position exposing said notch outside said well; and
    a dual-positioned detent mechanism for alternately holding said plunger in said first resting position and in a lingual, second resting position wherein said notch resides within said well and defines, in cooperation with said slot, a locked passage for said section of arch wire.

10. An orthodontic bracket, for securing a corrective arch wire to the labial surface area of a tooth, which comprises:
    a post associated with said bracket and having a lateral notch shaped and dimensioned to capture a section of said arch wire;
    a dual-positioned detent mechanism for alternately exposing an occluding access to said notch;

a solid body having a distal side and a well in said distal side; and wherein said post is slidingly engaged into said well and is alternately positionable by said detent mechanism in a notch-exposing position outside said well and in a locking position within said well.

11. The bracket of claim 10, wherein said body has a slot cut in said distal side and diametrically intersecting said well; and in said locking position, portions of said notch and slot line up to define a passageway commensurate with said section of arch wire.

12. The bracket of claim 11, wherein said detent mechanism comprises a compression spring positioned within said well to bias said post toward said notch-exposing position.

13. The bracket of claim 12, wherein said detent mechanism further comprises:

said well having a cylindrical wall section and a series of alternating short and long, axially oriented indentations in said well section;

an indexing ring having at least one peripheral key shaped and dimensioned to alternatly engage said short and long indentations; and means, associated with said post, for incrementally rotating said ring with each sliding movement of said post into said well.

14. The bracket of claim 12, which further comprises a base pad having a first face shaped and dimensioned to intimately contact said surface area of the tooth.

15. The bracket of claim 14, wherein said detent mechanism is housed in a lingual section of said well proximate said pad.

16. The bracket of claim 10, which further comprises a pair of spaced-apart tie-wings projecting laterally thereupon in a gingival direction.

17. The bracket of claim 16, which further comprises a second pair of spaced-apart tie-wings projecting laterally therefrom in a occlusal direction.

* * * * *